United States Patent
Onishi et al.

(10) Patent No.: US 7,169,955 B2
(45) Date of Patent: Jan. 30, 2007

(54) PERFLUOROISOPROPYLBENZENE DERIVATIVE

(75) Inventors: Masanobu Onishi, Tondabayashi (JP); Kenichi Ikeda, Izumi (JP); Takashi Shimaoka, Sakai (JP); Masanori Yoshida, Hashimoto (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 278 days.

(21) Appl. No.: 10/969,974

(22) Filed: Oct. 22, 2004

(65) Prior Publication Data
US 2005/0113567 A1 May 26, 2005

Related U.S. Application Data

(63) Continuation of application No. 10/182,549, filed on Sep. 11, 2002, now abandoned.

(30) Foreign Application Priority Data
Feb. 4, 2000 (JP) ............................. 2000-027982

(51) Int. Cl.
C07C 43/02 (2006.01)
C07C 63/00 (2006.01)

(52) U.S. Cl. ...................... 568/641; 562/480
(58) Field of Classification Search ............... 568/641, 568/480
See application file for complete search history.

(56) References Cited

U.S. PATENT DOCUMENTS

| | | | |
|---|---|---|---|
| 3,462,482 A | | 8/1969 | Farah et al. |
| 3,501,522 A | | 3/1970 | Farah et al. |
| 3,712,929 A | | 1/1973 | Middleton |
| 3,732,307 A | | 5/1973 | Middleton |
| 4,331,821 A | * | 5/1982 | Schubart et al. ............ 570/196 |
| 5,426,225 A | | 6/1995 | Kameswaran |
| 5,659,046 A | | 8/1997 | Kameswaran |
| 6,703,533 B1 | * | 3/2004 | Belen'Kii et al. .......... 570/156 |

FOREIGN PATENT DOCUMENTS

| | | |
|---|---|---|
| EP | 0082252 | 6/1983 |
| EP | 1 006102 | 6/2000 |
| HU | 214085 | 12/1997 |

OTHER PUBLICATIONS

Ishikawa et al "Dou wo mochiiru Houkoukan ka" Nippon Kanaku Gakkaishi 1973 No. 12 pp. 2351-2356.

Karnov et al "Formation of O-H-perfluoroalkylhensenes from system" Izy Akarl Nauk SSSR Ser Khim 1991 No. 11 pp. 2618-2623.

Klahunde et al "Activities of polyfluorinated hydrocarbons J Aryl geometry"J Amer Chem Soc 1972 vol. 94 No. 3 pp. 820-2420.

Shennard W A "Electronic properties of fluoroalkyl interaction"J Amer Chem Soc 1965 vol. 87 No. 11 pp. 2410-2420.

CA 129:15935, Sterlin et al. "Condensation of fluorinated carbonyl compounds with halobenzenes" J. Fluorine Chem. (1998), 89(2), pp. 137-139.

CA 78:43571, Kuroda et al. "Organic fluorine-silicon . . . methyldiethoxysilanes" Nippon Kagaku Kaishi (1972), (10), pp. 1876-1881.

CA 63:23651, Sheppard, w. "Electronic properties of fluoroalkyl . . . interaction" J. Amer. Chem. Society (1965), 87(11), pp. 2410-2420.

CA 63:23650, Ho et al. "Influence of substituent groups . . . N-nitrosoacetanilides" Tetrahedron (1965), 21(5), pp. 955-961.

* cited by examiner

Primary Examiner—Deborah C. Lambkin
(74) Attorney, Agent, or Firm—Paul E. White, Jr.; Manelli Denison & Selter PLLC

(57) ABSTRACT

Perfluoroisopropylbenzene derivatives of the general formula (I) or salts thereof, useful as intermediates or raw materials in the synthesis of various industrial materials including agricultural chemicals, drugs and surfactants:

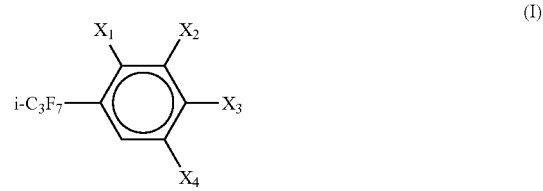

wherein $X_1$ is H, halogen, formyl, optionally halogenated $(C_1-C_6)$ alkyl, $(C_1-C_6)$ alkylthio, or the like; $X_2$ is H, halogen, formyl, hydroxyl, $(C_1-C_6)$ alkyl, —C(═O)—$R_1$ (wherein $R_1$ is H, halogen, hydroxyl, $(C_1-C_6)$ alkyl, or $NR_2R_3$, with $R_2$ and $R_3$ being each H, $C_{1-6}$ alkyl, or the like), or the like; $X_3$ is H, halogen, hydroxyl, cyano, isocyanate, hydrazino, diazo, —C(═O)—$R_1$, —$SO_2$—$R_4$ (wherein $R_4$ is halogen, hydroxyl, $(C_1-C_6)$ alkyl, or $NR_5R_6$, with $R_5$ and $R_6$ being each H or $(C_1-C_6)$ alkyl), or the like; and $X_4$ is H, halogen, $(C_1-C_6)$ alkyl, or $(C_1-C_6)$ alkoxy, with publicly known compounds being excepted.

21 Claims, No Drawings

PERFLUOROISOPROPYLBENZENE DERIVATIVE

This is a continuation of U.S. application Ser. No. 10/182,549 having the filing date of Sep. 11, 2002 now abandoned.

TECHNICAL FIELD

This invention relates to a novel perfluoroisopropylbenzene derivative or salts thereof.

BACKGROUND ART

Since perfluoroisopropylbenzene have a perfluoroalkyl group, which exhibits mainly physicochemically distinctive features, they are useful as intermediates or raw materials for synthesizing agricultural chemicals, medicines, dye stuffs surface active agents, wetting agents, dispersing agents, rubber materials, releasing agents, water and oil repelling agents, optical materials, gas separation membrane materials, resist materials, antifouling paints, weather-proofing paints, paper-converting agents, textile-treating agents, functional resins having such characteristics as heat resistance and weather resistance, antistatic agents, photographic toners, liquid crystal materials and solvents (refer, for example, to "Advanced Technology of Halogen Chemicals" published by CMC).

Heretofore, not many reports have been made on examples of production of perfluosoisopropylbenzenes.

Previously known methods in the literature for introducing a perfluoroisopropyl group into a benzene ring are, for example:

(a) a method of replacing a halogen in a halogenated benzenes by using 2-iodoheptafluoropropane in the presence of metallic copper, for example, methods described in (1) Tetrahedron, 25, 5921 (1969), (2) German Patent publication No. 2606982, (3) Journal Chem. Soc. Jpn., 1876 (1972), (4) J. Chem. Soc. Perkin Trans. 1, 661 (1980), and (5) Bull. Chem. Soc. Jpn., 65, 2141 (1992). These methods, however, are industrially disadvantageous in that prior introduction of a halogen atom to the appropriate position of benzenes is necessary, excess of copper is required and the reaction temperature is high. Moreover, depending on the kind of substituents of benzenes, the yield is low and good results are not obtained.

(b) a method of reacting hexafluoropropene on fluoronitrobenzenes in the presence of a fluorine anion, for example, the methods described in (1) J. Chem. Soc. C, 2221 (1968), (2) J. Soc. Org. Synth. Chem., Jpn., 27, 993 (1969), (3) J. Chem. Soc. Jpn., 198 (1976) and (4) Tetrahedron, 51, 13167 (1995). In these methods, however, the substrates which can be used are restricted to those which have been strongly activated by electron withdrawing groups, e.g., perfluoronitrobenzenes and dinitrofluorobenzenes, so that the methods are limited as to the substituent, structure, etc. of obtainable compounds.

(c) a method of reacting an unsubstituted or substituted phenyl Grignard reagent with hexafluoroacetone and then reacting 1-hydroxy-1-trifluoromethyl-2,2,2-trifluoroethylbenzenes thus obtained with an appropriate fluorinating agent, for example, the method described in Canadian Pat. No. 1,022,573. This method, however, is not always economically advantageous because it uses in the reaction industrially difficult-to-handle reagents, such as hydrofluoric acid and $SF_4$.

(d) a method of reacting (heptafluoroisopropyl) phenyliodonium trifluoromethanesulfonate with phenols to obtain perfluoroisopropylphenols, described in Bull. Chem. Soc. Jpn., 57, 3361 (1984). This method, however, is not promising for industrial practice owing to the use of expensive reagent and low selectivity as to the perfluoroisopropylated position of the compound obtained.

(e) a method of reacting iodobenzenes, in the presence of palladium catalyst, with a perfluoroisopropylzinc compound prepared from 2-iodoheptafluoropropane and zinc in the system, to obtain perfluoroisopropylbenzenes, described in Chemistry Letters, 137 (1982). This method, however, is not industrially advantageous owing to its reaction conditions wherein zinc is to be used and the reaction needs to be conducted under ultrasonic waves.

In the prior processes for producing perfluoroisopropylbenzenes, the intended compounds are produced by introducing a perfluoroisopropyl group into intended benzenes by the above-mentioned methods or by subjecting the perfluoroisopropylbenzenes produced by the above-mentioned methods to structural transformation. Both processes are not satisfactory in practice.

Since previous processes are thus not suited to practical use, few examples are known of the production of perfluoroisopropylbenzenes. However, since the perfluoroisopropyl group is a substituent having distinctive features both physically and biochemically, the literature in several fields describes the usefulness of benzenes having a perfluoroisopropyl group introduced thereinto.

As to benzoic acids having a perfluoroisopropyl group as a substituent, for example, JP-A-9-319147 discloses that phthalic acids having a perfluoroisopropyl group on the benzene ring is useful as a positively chargeable charge-controlling agent and as a toner for electrostatic image developing, and JP-A-59-69755 discloses that some of the benzoic amides having a perfluoroisopropyl group are useful as a photographic cyan coupler.

As to perfluoroisopropylbenzenesulfonic acids, for exmaple, U.S. Pat. No. 3,501,522 describes that some of the sulfonic acids and their salts are useful as a wetting agent and dispersing agent and discloses a method of producing 4-heptafluorobenzoic acid from 1-methyl-4-(1-trifluoromethyl-1-hydroxy-2,2,2-trifluoroethyl)benzene as the starting material via 1-methyl-4-heptafluoroisopropylbenzene. This method, however, is industrially disadvantageous because it uses highly toxic reagent as $SF_4$ and chromic acid and hence results in high cost of production facilities and waste proposal.

In the previous known methods, in general, it is necessary to introduce a halogen atom beforehand to the position into which a perfluoroisopropyl group is to be introduced, or the benzenes to which a perfluoroisopropyl group can be introduced are limited to those having a certain substituent, such as phenols and nitrobenzenes. Consequently, the kinds of substituents of perfluoroisopropylbenzenes produced in the past are small in number. Furthermore, all of the methods described above are not suited to mass production. Therefore, in spite of the perfluoroisopropyl group being a substituent which has physically distinctive features and is promising for its usefulness in various fields, not much perfluoroisopropylbenzenes have hitherto been produced.

DISCLOSURE OF THE INVENTION

The objects of this invention are to provide a novel and useful perfluoroisopropylbenzene derivative or the salts thereof, and to provide a process for producing, in the manner described in JP-11-229304, various perfluoroisopropylbenzene derivatives in a simple manner and with good yield by using easily producible perfluoroisopropylanilines, and various novel perfluoroisopropylbenzene derivatives.

According to this invention, there are provided a perfluoroisopropylbenzene derivative represented by the formula (I) or salts thereof:

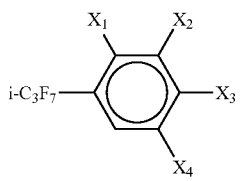

wherein $X_1$ is a hydrogen atom, halogen atom, formyl group, $(C_1-C_6)$alkyl group, halo $(C_1-C_6)$alkyl group, $(C_1-C_6)$alkoxy group, $(C_1-C_6)$alkylthio group, hydroxy$(C_1-C_6)$alkyl group or $(C_1-C_6)$alkylcarbonyloxy$(C_1-C_6)$alkyl group; $X_2$ is a hydrogen atom, halogen atom, formyl group, hydroxy group, $(C_1-C_6)$alkyl group, halo$(C_1-C_6)$alkyl group, $(C_1-C_6)$alkoxy group, $(C_1-C_6)$alkylthio group, $(C_1-C_6)$alkylsulfinyl group, $(C_1-C_6)$alkylsulfonyl group, hydroxy$(C_1-C_6)$alkyl group or $-C(=O)-R_1$ (wherein $R_1$ is a hydrogen atom, halogen atom, hydroxy group, $(C_1-C_6)$alkyl group, $(C_1-C_6)$alkoxy group or $NR_2R_3$ (wherein $R_2$ and $R_3$ may be the same or different and are each a hydrogen atom, $(C_1-C_6)$alkyl group or $(C_1-C_6)$alkoxy group)); $X_3$ is a hydrogen atom, halogen atom, hydroxy group, cyano group, isocyanate group, isothiocyanate group, hydrazino group, diazo group, mercapto group, $(C_1-C_6)$alkoxy group, $(C_1-C_6)$alkylthio group, $-C(=O)-R_1$ (wherein $R_1$ is the same as defined above) or $-SO_2-R_4$ (wherein $R_4$ is a halogen atom, hydroxy group, $(C_1-C_6)$alkyl group or $NR_5R_6$ (wherein $R_5$ and $R_6$ may be the same or different and are each a hydrogen atom or $(C_1-C_6)$alkyl group)); and $X_4$ is a hydrogen atom, halogen atom, $(C_1-C_6)$alkyl group or $(C_1-C_6)$alkoxy group; provided that (1) when $X_1$, $X_2$ and $X_4$ are each a hydrogen atom, then $X_3$ is not a hydroxycarbonyl group or methoxycarboxyl group, (2) when $X_1$ and $X_4$ are each a hydrogen atom and $X_2$ is a formyl group, then $X_3$ is not a methoxy group, (3) when any one of $X_1$, $X_2$ and $X_3$ is a methoxy group, then $X_4$ and the remaining two of $X_1$, $X_2$ and $X_3$ are not each a hydrogen atom, (4) when any one of $X_2$ and $X_3$ is a hydroxyl group, then $X_1$, $X_4$ and the remaining one of $X_2$ and $X_3$ are not each a hydrogen atom, (5) when any one of $X_1$, $X_2$, $X_3$ and $X_4$ is a fluorine atom, then the remaining three of $X_1$, $X_2$, $X_3$ and $X_4$ are not each a hydrogen atom, (6) when $X_1$, $X_2$ and $X_4$ are each a hydrogen atom, then $X_3$ is not a chlorine atom, bromine atom or iodine atom, (7) when any one of $X_1$, $X_2$, $X_3$ and $X_4$ is a methyl group, then the remaining three of $X_1$, $X_2$, $X_3$ and $X_4$ are not each a hydrogen atom, (8) when $X_1$, $X_2$ and $X_4$ are each a hydrogen atom, then $X_3$ is not an isopropyl group or chloromethyl group, (9) when $X_1$, $X_3$ and $X_4$ are each a hydrogen atom, then $X_2$ is not a trifluoromethyl group, and

(10) when $X_1$ and $X_4$ are each a methyl group and $X_2$ is a hydrogen atom, then $X_3$ is not a hydrogen atom or heptafluoroisopropyl group.

MODE FOR CARRYING OUT THE INVENTION

As to the definition of the formula (I), which represents the perfluoroisopropylbenzene derivative of this invention, in the definition of its respective substituents, "i" means iso, "sec-" means secondary and "t" means tertiary, an "alkyl group" or "alkyl", which indicates an alkyl moiety, may be both of a straight chain or a branched chain, and a "$(C_1-C_6)$ alkyl group" refers to an alkyl group having 1–6 carbon atoms, which may be, for example, a methyl group, ethyl group, propyl group, i-propyl group, butyl group, sec-butyl group, t-butyl group, neopentyl group, 1,2-dimethylpropyl group, hexyl group and heptyl group.

A "halogen atom" indicates a chlorine atom, bromine atom, iodine atom or fluorine atom; a "halo$(C_1-C_6)$alkyl group", which may be the same or different, indicates a straight or branched chain alkyl group having 1–6 carbon atoms wherein at least one of the hydrogen atoms has been substituted with a halogen atom, and may be, for example, a difluoromethyl group, trifluoromethyl group, chloromethyl group, bromomethyl group, 1-fluoroethyl group, 1-chloroethyl group, 1-bromoethyl group, 2-chloroethyl group, 2-bromoethyl group, 2,2,2-trifluoroethyl group, 3-chlorobutyl group, 3-bromobutyl group, 1-chloropentyl group, 1-chlorohexyl group and 6-bromohexyl group.

An "alkoxy group" or "alkoxy" moiety means a straight or branched chain alkoxy group, and a "$(C_1-C_6)$alkoxy group" refers, for example, to a methoxy group, ethoxy group, i-propoxy group, sec-butoxy group, t-butoxy group, 1,2-dimethylpropoxy group and hexyloxy group.

A "halo$(C_1-C_6)$alkoxy group", which may be the same or different, indicates a straight or branched chain alkoxy group having 1–6 carbon atoms wherein at least one of the hydrogen atoms has been substituted with a halogen atom, and may be, for example, a difluoromethoxy group, trifluoromethoxy group, 2-chloroethoxy group, 2-bromoethoxy group, 2,2,2-trifluoroethoxy group, pentafluoroethoxy group, 1,1,2,2-tetrafluoroethoxy group, 3-chlorobutoxy group, 3-bromobutoxy group, 1-chloropentyloxy group, 1-chlorohexyloxy group and 6-bromohexyloxy group.

A "$(C_1-C_6)$alkylthio group" refers to a straight or branched chain alkylthio group having 1–6 carbon atoms and may be, for example, a methylthio group, ethylthio group, i-propylthio group, sec-butylthio group, t-butylthio group and hexylthio group.

A "halo$(C_1-C_6)$alkylthio group", which may be the same or different, refers to a straight or branched chain alkylthio group having 1–6 carbon atoms wherein at least one of the hydrogen atoms has been substituted with a halogen atom, and may be, for example, a difluoromethylthio group, trifluoromethylthio group, 2,2,2-trifluoroethylthio group, 1,1,2,2-tetrafluoroethylthio group, 2-chloroethylthio group and 3-bromoethylthio group.

A "hydroxy$(C_1-C_6)$alkyl group", which may be the same or different, refers to a straight or branched chain alkyl group having 1–6 carbon atoms wherein at least one of the hydrogen atoms has been substituted with a hydroxy group, and may be, for example, a hydroxymethyl group, 1-hydroxyethyl group and 2-hydroxyethyl group.

Some examples of the representative processes for producing the perfluoroisopropylbenzene derivative represented by the formula (I) of this invention are described below, but the invention is not limited thereby.

[Production process 1]

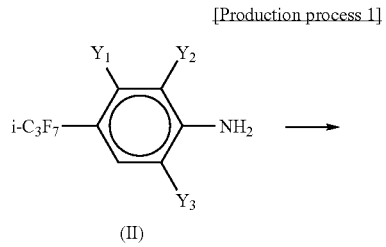

(II)

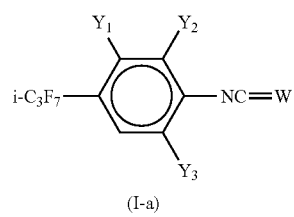

(I-a)

wherein $Y_1$, $Y_2$ and $Y_3$ may be the same or different and are each a hydrogen atom, hydroxy group, chlorine atom, bromine atom, fluorine atom, ($C_1$–$C_6$)alkyl group, ($C_1$–$C_6$) alkoxy group or hydroxy($C_1$–$C_6$)alkyl group, and W is an oxygen atom or sulfur atom.

By reacting an aniline represented by the formula (II) with phosgene, TCF (trichlorochloroformate), etc. in the presence or absence of an inert solvent in the presence or absence of a catalyst, such as DMAP (4-dimethylaminopyridine), the perfluoroisopropylbenzene derivative represented by the formula (I-a) can be produced.

In the perfluoroisopropylbenzene derivatives, the compounds wherein W is an oxygen atom may be produced, for example, according to the methods described in J. Am. Chem. Soc., (1937) 79, p. 1236, Org. Synth. II, (1943) p. 453, J. Org. Chem., (1966) 31, p. 596, Angew. Chem. Int. Ed. Engl (1987), 26(9), p. 894, and Angew. Chem. Int. Ed. Engl (1995), 34(22), p. 2497.

The compounds wherein W is a sulfur atom may be produced, for example, according to the methods described in J. Chem. Soc. (1942) p. 374, J. Am. Chem. Soc. (1946) 68, p. 2506, Liebigs Ann. Chem. (1962) 657, 98 and Bull. Chem. Soc. Jpn. (1975) 48, p. 2981.

The anilines represented by the formula (II), a starting material, may be produced according to the method described in JP-11-338707.

-continued

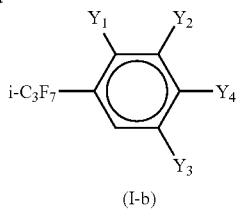

(I-b)

wherein $Y_1$, $Y_2$ and $Y_3$ are the same as defined above, and $Y_4$ is a hydrogen atom, halogen atom, hydroxy group, sulfonyl halide group or hydrazino group or the salt thereof.

By reacting a diazonium salt of an aniline, obtained by reacting an aniline represented by the formula (II) with sodium nitrite, etc. by using an acidic solvent, and a metal halide with each other in the presence or absence of a metal catalyst, such as copper, the perfluoroisopropylbenzene derivative represented by the formula (I-b) can be produced.

In the present process, among the perfluoroisopropylbenzene derivatives represented by the formula (I-b), the compounds wherein $Y_4$ is a hydrogen atom may be produced, for example, according to the methods described in J. Chem. Soc., p. 2095 (1949): Org. React., 2, p. 262 (1944), Org. Synth., (1955) III, 295 and J. Am. Chem., 83, p. 1251 (1961), those wherein $Y_4$ is a fluorine atom according to the method described in Org. React., 5, p. 193 (1949) and J. Org. Chem., 36, p. 63 (1971), those wherein $Y_4$ is a chlorine atom according to the method described in Org. Synth., I. p. 170 (1941) and J. Chem. Soc., p. 819 (1945), those wherein $Y_4$ is a bromine atom according to the method described in Org. Synth. III, p. 185 (1955) and J. Org. Chem., 23, p. 1139 (1958) and those wherein $Y_4$ is an iodine atom according to the method described in J. Org. Chem. 3, p. 55 (1938), J. Am. Chem. Soc. 70, p. 157 (1948), J. Am. Chem. Soc. 92, p. 2175 (1970) and J. Am. Chem. Soc. 93, p. 4845 (1971).

The compounds wherein $Y_4$ is a hydroxy group may be produced, for example, according to the methods described in Org. Synth., I, p. 404 (1941), Org. Synth., III, p. 130 (1955), Can. J. Chem, 41, p. 1653 (1963) and J. Org. Chem., 32, p. 3844 (1967), those wherein $Y_4$ is a sulfonyl halide group according to the methods described in J. Prakt. Chem. [2]152, p. 251 (1939) and Recl. Trav. Chim. Pays-Bas., 84, p. 22 (1965), and those wherein $Y_4$ is a hydrazino group or its salt according to the method described in Org. Synth., I, p. 442 (1941).

In the perfluoroisopropylbenzene derivatives, the compounds wherein $Y_4$ is an aldehyde group may be produced by oxidizing the compounds wherein $Y_4$ is a hydroxy group obtained by the above-mentioned methods, according to a conventional method.

[Production process 2]

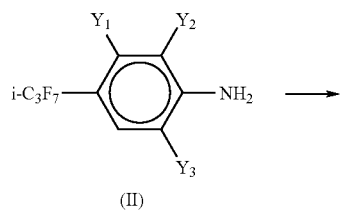

(II)

[Production process 3]

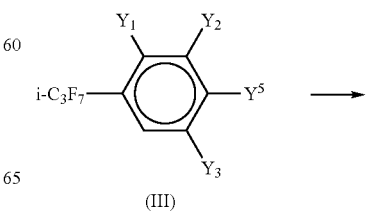

(III)

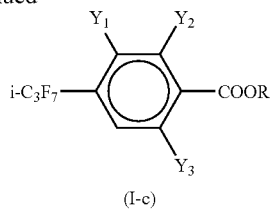

(I-c)

wherein $Y_1$, $Y_2$ and $Y_3$ are the same as defined above, $Y_5$ is a chlorine atom, iodine atom or bromine atom, and R is a hydrogen atom or ($C_1$–$C_{12}$)alkyl group.

By reacting the halogenated benzenes represented by the formula (III) with carbon monoxide in the presence of a base, organic phosphorus compound, such as triphenylphosphine and bisdiphenyl-phosphinobutane, transition metal, such as palladium, nickel and cobalt, or its complex, and an inert solvent, the perfluoroisopropylbenzene derivatives represented by the formula (I-c) can be produced.

This process can be conducted, for example, according to the methods described in Bull. Chem. Soc. Jpn., 48, p. 2075 (1975) and J. Am. Chem. Soc. 111, p. 8742 (1989).

By starting from the perfluoroisopropylbenzene derivatives represented by the formula (I-c) and through the method described below, perfluoroisopropylbenzene derivatives represented by the formulas (I-d), (I-e), (I-f) and (I-g) can be produced.

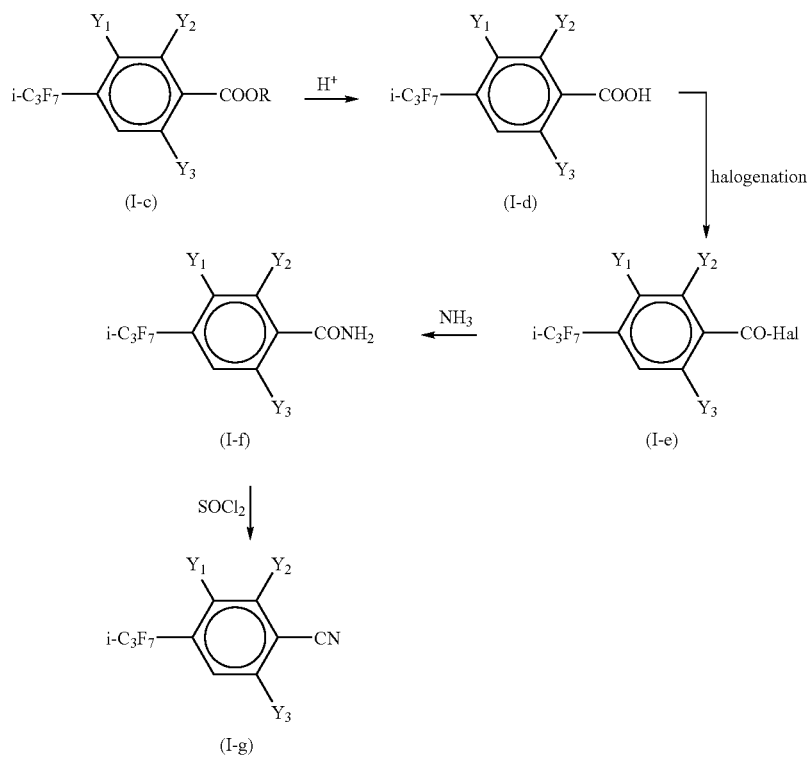

wherein $Y_1$, $Y_2$, $Y_3$ and R are the same as defined above, and Hal is a halogen atom.

The reactions shown above may be conducted by conventional methods.

EXAMPLES

Some representative examples of this invention are described below with reference to Examples, but the invention is not limited thereto.

1. Preparation of Halobenzenes

Example 1

Preparation of 1-chloro-4-heptafluoroisopropylbenzene

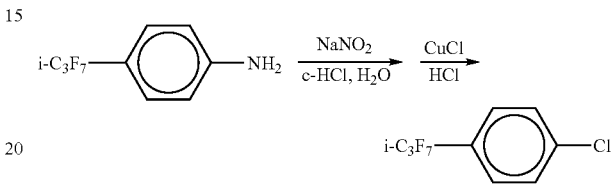

Concentrated hydrochloric acid (30 ml) was diluted with water (10 ml), and 4-heptafluoro-isopropylaniline (10 g, 38.3 mmols) was added thereto to form a suspension. Then, aqueous sodium nitrite (2.9 g, 42 mmols) solution (10 ml) was slowly added thereto so that the reaction temperature might be not higher than 10° C. After completion of the addition, the reaction mixture was stirred for further 20 minutes. The resulting diazonium salt solution was slowly added at room temperature to a solution of copper chloride (I) (5.7 g, 57 mmols) in hydrochloric acid (25 ml) prepared separately. Then the reaction mixture was stirred at room-temperature for 30 minutes, heated for 1 hour, then cooled to room temperature, hexane was added to the reaction mixture to separate an organic layer, the organic layer was washed once with water, twice with an aqueous sodium thiosulfate solution and once with a saturated aqueous sodium chloride solution, dried with anhydrous sodium sulfate, and then concentrated under reduced pressure to obtain a crude product (8.6 g, yield (crude) 80%) of the intended compound.

Physical property: $^1$H-NMR δ(CDCl$_3$): 7.49(d, 2H), 8.07 (d, 2H).

Example 2

Preparation of 1-bromo-2-fluoro-4-heptafluoroisopropylbenzene

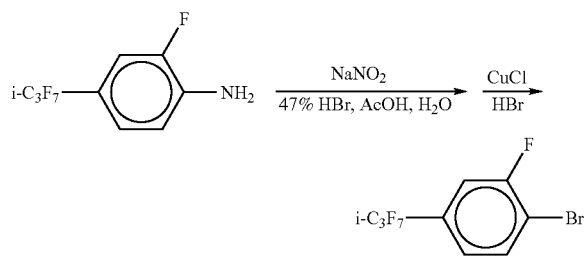

An aqueous 47% hydrogen bromide solution (50 ml) was diluted with water (15 ml), and 2-fluoro-4-heptafluoroisopropylaniline (15.7 g, 56 mmols) was added thereto. Then, an aqueous sodium nitrite (4.1 g, 59 mmols) solution (20 ml) was slowly added thereto so that the reaction temperature might be not higher than 10° C. After completion of the addition, the reaction mixture was stirred for further 20 minutes. The resulting diazonium salt solution was added at a time at 65° C. to a separately prepared solution of copper bromide (I) (4.0 g, 26 mmols) in an aqueous 47% hydrogen bromide solution (40 ml), the resulting reaction mixture was stirred at 60–80° C. for 2 hours, then cooled to room temperature, hexane was added thereto to separate an organic layer, the organic layer was washed once with water, twice with an aqueous sodium thiosulfate solution and once with a saturated aqueous sodium chloride solution. Then the organic layer was dried with anhydrous sodium sulfate and concentrated under reduced pressure to obtain a crude product (15 g, yield (crude) 78%) of the intended compound.

Physical property: $^1$H-NMR δ(CDCl$_3$): 7.294(d, 1H), 7.39(d, 1H), 7.72(t, 1H).

nD 1.4318 (21.3° C.)

Example 3

Preparation of 1-bromo-3-heptafluoroisopropylbenzene

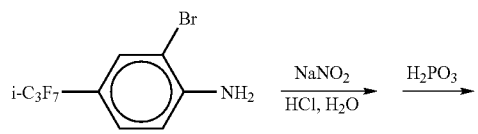

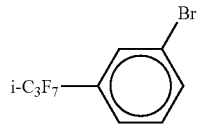

An aqueous hydrochloric acid solution (60 ml) was diluted with water (20 ml), and 2-bromo-4-heptafluoroisopropylaniline (20 g, 59 mmols) was added thereto to form a suspension. Then an aqueous sodium nitrite (4.3 g, 62 mmols) solution (15 ml) was slowly added to the suspension so that the reaction temperature might be 5° C. After completion of the addition, the reaction mixture was stirred for further 30 minutes. To the resulting diazonium salt solution was added dropwise at 5–10° C. hypophosphorous acid (35 ml) in several portions over 1 hour. After completion of the addition, the reaction mixture was further stirred at room temperature for 3 hours, then hexane was added thereto to separate an organic layer, the organic layer was washed once with water and once with an aqueous saturated sodium chloride solution, dried with anhydrous sodium sulfate, then concentrated under reduced pressure, and the resulting residue was purified by column chromatography to obtain the intended product (17.2 g, yield (crude) 90%).

Physical property: $^1$H-NMR δ(CDCl$_3$): 7.39(t, 1H), 7.554 (d, 1H), 7.69(m, 1H), 7.76(s, 1H).

Example 4

Preparation of 4-heptafluoroisopropyliodobenzene

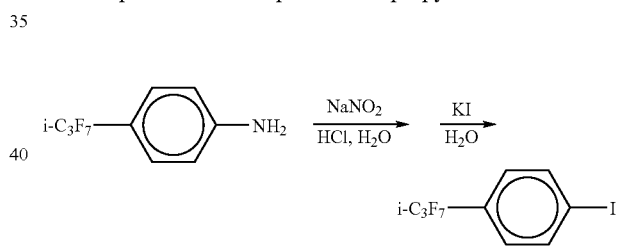

In an ice bath, concentrated sulfuric acid (7.5 g, 76.6 mmols) was diluted with water (30 ml), and 4-heptafluoroisopropylaniline (10 g, 38.3 mmols) was added thereto. Then an aqueous sodium nitrite (2.9 g, 42 mmols) solution (20 ml) was slowly added so that the reaction temperature might be not higher than 0° C., the reaction mixture was further stirred for 20 minutes, and then concentrated sulfuric acid (3.8 g) was added. The resulting diazonium salt solution was slowly added at room temperature to a separately prepared aqueous potassium iodide (9.5 g, 57.5 mmols) solution (20 ml). Then the resulting mixture was heated under reflux for 1 hour, then cooled to room temperature, hexane was added thereto to separate an organic layer, the organic layer was washed once with water, twice with an aqueous sodium thiosulfate solution and once with an aqueous saturated sodium chloride solution, dried with anhydrous sodium sulfate, and then concentrated under reduced pressure to obtain a crude product (13 g, yield (crude) 87%) of the intended compound.

In the same manner as above, the following perfluoroisopropylbenzene derivatives were obtained.

1-chloro-3-fluoro-4-heptafluoroisopropylbenzene

Physical property: $^1$H-NMR δ(CDCl$_3$); 7.23–7.33(m, 2H), 7.56(t, 1H),
$^{19}$F-NMR δ(CDCl$_3$); −75.82(6F), −106.73 (1F), −178.6 (1F).

1-chloro-2,6-dimethyl-4-heptafluoroisopropylbenzene

Physical property: $^1$H-NMR δ(CDCl$_3$); 2.44(s, 6H), 7.305 (s, 2H).

1-chloro-4-heptafluoroisopropyl-2-methylbenzene

Physical property: $^1$H-NMR δ(CDCl$_3$); 2.45(s, 3H), 7.38 (d, 1H), 7.46(m, 2H).

1-chloro-4-heptafluoroisopropyl-2-methoxybenzene

Physical property: $^1$H-NMR δ(CDCl$_3$); 3.95(s, 3H), 7.12 (s, 1H), 7.14(d, 1H), 7.50(d, 1H).

1-bromo-4-heptafluoroisopropyl-2-methylbenzene

Physical property: $^1$H-NMR δ(CDCl$_3$); 2.48(s, 3H), 7.27 (d, 1H), 7.45(s, 1H), 7.66(d, 1H).

1-bromo-4-heptafluoroisopropyl-3-methylbenzene

Physical property: $^1$H-NMR δ(CDCl$_3$); 2.50(d, 3H), 7.34 (d, 1H), 7.42(d, 1H), 7.46(s, 1H).

1-bromo-2,6-dimethyl-4-heptafluoroisopropylbenzene

Physical property: $^1$H-NMR δ(CDCl$_3$); 2.48(s, 6H), 7.29 (s, 2H).

1-bromo-4-heptafluoroisopropyl-2-methoxybenzene

Physical property: $^1$H-NMR δ(CDCl$_3$); 3.944(s, 3H), 7.08 (brs, 2H), 7.67(d, 1H).

1-bromo-3-fluoro-4-heptafluoroisopropylbenzene

Physical property: $^1$H-NMR δ(CDCl$_3$); 7.39–7.52(m, 3H).
$^{19}$F-NMR δ(CDCl$_3$); −75.77(6F), −106.64(1F), −178.61 (1F).

1-bromo-4-heptafluoroisopropyl-2-methylthiobenzene

Physical property: $^1$H-NMR δ(CDCl$_3$); 2.51(s, 3H), 7.21 (m, 1H), 7.285(s, 1H), 7.645(d, 1H).

1-bromo-2,6-dichloro-4-heptafluoroisopropylbenzene

Physical property: $^1$H-NMR δ(CDCl$_3$); 7.604(s, 2H).
$^{19}$F-NMR δ(CDCl$_3$); −75.98(6F), −182.61(1F).

1-iodo-4-heptafluoroisopropyl-3-methylbenzene

Physical property: $^1$H-NMR δ(CDCl$_3$); 2.47(d, 3H), 7.18 (d, 1H), 7.62(d, 1H), 7.68(s, 1H).
nD 1.4142 (24.2° C.)

1-iodo-4-heptafluoroisopropyl-2-methylbenzene

Physical property: $^1$H-NMR δ(CDCl$_3$); 2.504(s, 3H), 7.10 (d, 1H), 7.44(s, 1H), 7.94(d, 1H).

1-iodo-2,6-dimethyl-4-heptafluoroisopropylbenzene

Physical property: $^1$H-NMR δ(CDCl$_3$); 2.54(s, 6H), 7.26 (s, 2H).
$^{19}$F-NMR δ(CDCl$_3$); −76.15(d, 7F), −183.28(m, 1F).

1-iodo-4-heptafluoroisopropyl-2-methylbenzene

Physical property: $^1$H-NMR δ(CDCl$_3$); 2.51(s, 3H), 7.10 (d, 1H), 7.444(s, 1H), 7.94(d, 1H).

1-iodo-4-heptafluoroisopropyl-2-methylthiobenzene

Physical property: $^1$H-NMR δ(CDCl$_3$); 2.50(s, 3H), 7.06 (d, 1H), 7.235(s, 1H), 7.91(d, 1H).

1-iodo-4-heptafluoroisopropyl-2-methoxybenzene

Physical property: $^1$H-NMR δ(CDCl$_3$); 3.93(s, 3H), 6.94 (d, 1H), 6.98(s, 1H), 7.90(d, 1H).

2. Preparation of alkylbenzenes

Example 5

Preparation of 1-methyl-2-heptafluoroisopropylbenzene

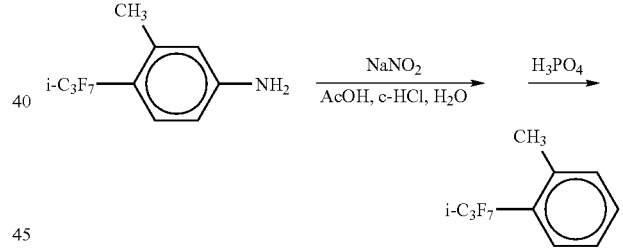

In an ice bath, concentrated hydrochloric acid (90 ml) was diluted with water (30 ml), and a solution of 4-heptafluoroisopropyl-3-methylaniline (30 g, 109 mmols) in glacial acetic acid (30 ml) was added thereto. Then, an aqueous sodium nitrite (8 g, 115 mmols) solution (15 ml) was slowly added so that the reaction temperature might not be higher than 5° C. After completion of the addition, the reaction mixture was further stirred for 1 hour, hypophosphrous acid (50 ml) was added, the temperature of the mixture was slowly increased, and the mixture was stirred at room temperature for 15 hours. Then hexane was added to the mixture to separate an organic layer, the organic layer was washed twice with water, once with an aqueous saturated sodium hydrogen carbonate solution and once with an aqueous saturated sodium chloride solution, dried with anhydrous sodium sulfate, and concentrated under reduced pressure to obtain a crude product (19 g) of the intended compound.

According to similar reactions, the following compounds were prepared.

1-methyl-3-heptafluoroisopropylbenzene

Physical property: $^1$H-NMR δ(CDCl$_3$); 2.42(s, 3H), 7.35–7.41(m-4H).

1,2-dimethyl-3-heptafluoroisopropylbenzene

Physical property: $^1$H-NMR δ(CDCl$_3$); 2.35(s, 3H), 2.40 (d, 3H), 7.13–7.19(m, 1H), 7.29–7.63(m, 2H).

1-ethyl-3-heptafluoroisopropylbenzene

Physical property: $^1$H-NMR δ(CDCl$_3$); 1.27(t, 3H), 2.73 (dd, 2H), 7.37–7.48(m, 4H).
$^{19}$F-NMR δ(CDCl$_3$); −76.23(d, 7F), −183.08(m, 1F).

1-chloromethyl-2-heptafluoroisopropylbenzene

Physical property: $^1$H-NMR δ(CDCl$_3$); 4.79(d, 2H), 7.44 (m, 1H), 7.52–7.63(m, 3H).

1-methyl-2-heptafluoroisopropyl-5-methylthiobenzene

Physical property: $^1$H-NMR δ(CDCl$_3$); 2.49(d, 3H), 2.495(s, 3H), 7.09(s, 1H), 7.11(d, 1H), 7.37(d, 1H).

2-heptafluoroisopropylbenzyl alcohol

Physical property: $^1$H-NMR δ(CDCl$_3$); 4.925(d, 2H), 7.41(d, 1H), 7.51–7.59(m, 2H), 7.81(d, 1H).

1-methyl-2-heptafluoroisopropyl-5-methoxybenzene

Physical property: $^1$H-NMR δ(CDCl$_3$); 2.49(d, 3H), 3.824(s, 3H), 6.78(s, 1H), 6.79(d, 1H), 7.40(d, 1H).
nD 1.4114 (24.2° C.)

2'-heptafluoroisopropylbenzyl acetate

Physical property: $^1$H-NMR δ(CDCl$_3$); 2.125(s, 3H), 5.32 (d, 2H), 7.44(m, 1H), 7.51–7.59(m, 3H).

1-bromomethyl-2-heptafluoroisopropylbenzene

Physical property: $^1$H-NMR δ(CDCl$_3$); 4.68(d, 2H), 7.40–7.45(m, 1H), 7.50–7.58(m, 3H).

3. Preparation of benzoic acids

Example 7

Preparation of methyl 4-heptafluoroisopropyl-3-methylbenzoate

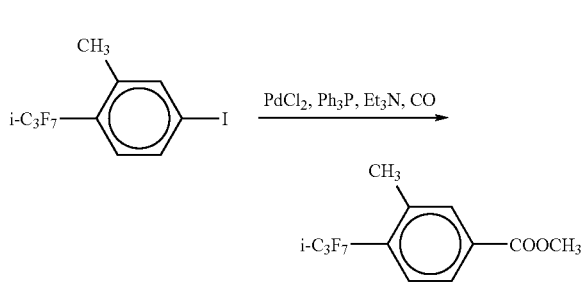

In an autoclave, 1-iodo-4-heptafluoroisopropyl-3-methylbenzene (1.0 g, 2.6 mmols), palladium chloride (10 ml, 2 mol %), triphenylphosphine (54 g, 8 mol %) and triethylamine (0.52 g, 5.2 mmols) were suspended in methanol (10 ml). Then, the inner atmosphere of the autoclave was replaced by carbon monoxide, and the pressure in the vessel was brought to about 14 atm. The suspension in the vessel was heated to about 120° and stirred for 8 hours. Then the reaction mixture was cooled to room temperature, the insolubles were filtered off, and the filtrate was concentrated and then purified by silica gel column chromatography (hexane:ethyl acetate=9:1) to obtain the intended product (0.77 g, yield 94%).

Example 8

Preparation of ethyl 2-fluoro-4-heptafluoroisopropylbenzoate

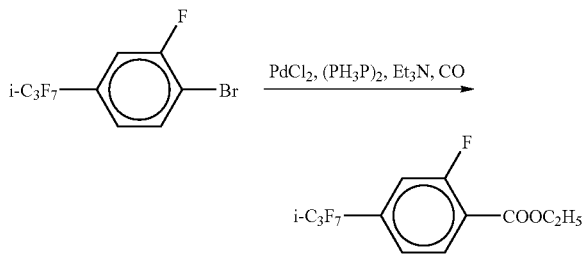

In an autoclave, 1-bromo-2-fluoro-4-heptafluoroisopropylbenzene (10.0 g, 29 mmols), dichlorobis(triphenylphosphine)palladium (1.0 g, 5 mol %) and triethylamine (3.5 g, 35 mmols) were suspended in ethanol (60 ml). Then, the inner atmosphere of the autoclave was repalced by carbon monoxide, and the pressure in the vessel was brought to about 14 atm. The suspension in the vessel was heated to about 120° C. and stirred for about 8 hours. Then the reaction mixture was cooled to room temperature, the insolubles were filtered off, and the filtrate was concentrated and then purified by silica gel column chromatography (hexane:ethyl acetate=9:1) to obtain the intended product (7.4 g, yield 75%).

Example 9

Preparation of methyl 4-heptafluoroisopropylbenzoate

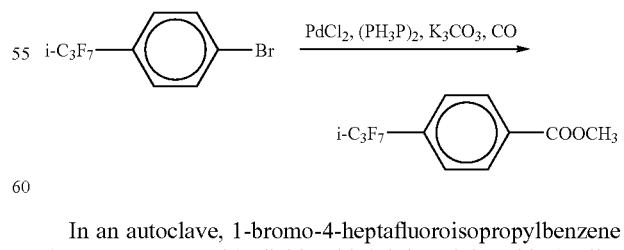

In an autoclave, 1-bromo-4-heptafluoroisopropylbenzene (11.8 g, 31.7 mmols), dichlorobis(triphenylphosphine)palladium (1.1 g, 5 mol %) and potassium carbonate (3.2 g, 31.7 mmols) were suspended in methanol (50 ml). Then the inner atmosphere of the autoclave was replaced by carbon monoxide and the pressure in the vessel was brought to about 14 atm. The suspension in the vessel was heated to about 110° C. and stirred for 6 hours. Then the reaction mixture was cooled to room temperature, then the insolubles were filtered off, and the filtrate was concentrated and then purified by silica gel column chromatography (hexane:ethyl acetate=9: 1) to obtain the intended product (7.4 g, yield 75%).

In the same manner as described abovew, the following compounds were prepared.

methyl 2,6-dimethyl-4-heptafluoroisopropylbenzoate

Physical property: $^1$H-NMR δ(CDCl$_3$); 2.37(s, 6H), 3.94 (s, 3H), 7.27(s, 2H).

methyl 4-heptafluoroisopropyl-2-methoxybenzoate

Physical property: $^1$H-NMR δ(CDCl$_3$); 3.92(s, 3H), 3.95 (s, 3H), 7.19(s, 1H), 7.21(d, 1H), 7.87(d, 1H).

methyl 4-heptafluoroisopropyl-2-methylbenzoate

Physical property: m.p. 39–40° C.

ethyl 2,6-dimethyl-4-heptafluoroisopropylbenzoate

Physical property: $^1$H-NMR δ(CDCl$_3$); 1.41(t, 3H), 2.38 (s, 6H), 4.43(dd, 2H), 7.33(s, 2H).

methyl 3-fluoro-4-heptafluoroisopropylbenzoate

Physical property: $^1$H-NMR δ(CDCl$_3$); 3.965(s, 3H), 7.72 (t, 1H), 7.86(m, 1H), 7.96(m, 1H).

methyl 4-heptafluoroisopropyl-3-methylbenzoate

Physical property: $^1$H-NMR δ(CDCl$_3$); 2.59(d, 3H), 3.94 (s, 3H), 7.56(d, 1H), 7.914(d, 1H), 7.955(s, 1H).

methyl 4-heptafluoroisopropyl-2-methylsulfonylbenzoate

Physical property: $^1$H-NMR δ(CDCl$_3$); 3.38(s, 3H), 4.014 (s, 3H), 7.86(d, 1H), 7.945(d, 1H), 8.38(s, 1H).
nD 1.4450 (27.2° C.)

Comparison with Prior Processes Relating to Benzoic Acids

U.S. Pat. No. 3,462,482 describes that some benzoic anilides having a heptafluoroisopropyl group, for example, 4-(heptafluoroisopropyl)benz-4-chloroanilide, are useful as a herbicide, pesticide and acaricide. It also discloses a process for producing 4-heptafluoroisopropylbenzoic acid used as a starting material therefor. In this process, 4-heptafluorobenzoic acid is prepared via 1-methyl-4-heptafluoroisopropylbenzene from 1-methyl-4-(1-trifluoromethyl-1-hydroxy-2,2,2-trifluoroethyl)benzene as the starting material. This process, however, uses highly toxic compounds such as SF$_4$ and chromic acid in the production and hence is not satisfactory for practical use.

According to the process of this invention, 4-heptafluoroisopropylbenzoic acid can be produced via 1-cyano-4-heptafluoroisopropylbenzene or 1-halo-4-heptafluoroisopropylbenzene (wherein "halo" denotes a chlorine atom, bromine atom or iodine atom) by using 4-heptafluoroisopropylaniline as the starting material; thus, the process is more suited to practical use.

Example 10

Preparation of 4-heptafluoroisopropylbenzoic acid

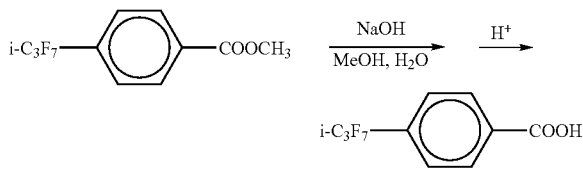

In an ice bath, a solution of sodium hydroxide (0.1 g, 2.5 mmols) dissolved in water (4 ml) was added dropwise to a solution of methyl 4-heptafluoroisopropylbenzoate (0.5 g, 1.5 mmols) in ethanol (4 ml). The resulting mixture was stirred for about 2 hours, then hexane and water were added thereto, and an aqueous layer was separated. The aqueous layer was made to acidify by addition of 3N hydrochloric acid, and ethyl acetate was added thereto to separate an organic layer. The organic layer was dried with anhydrous sodium sulfate, and then concentrated under reduced pressure to obtain the intended product (9.0 g, yield 93%).

Example 11

Preparation of 4-heptafluoroisopropyl-3-methylbenzoic acid

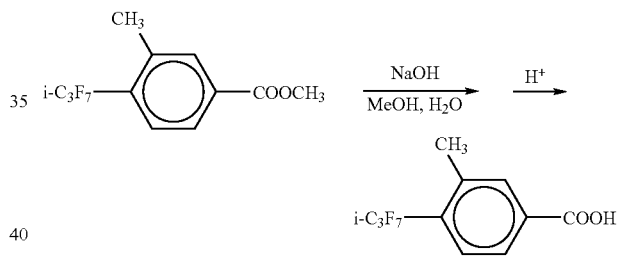

In an ice bath, a solution of sodium hydroxide (0.1 g, 2.5 mmols) dissolved in water (4 ml) was added dropwise to a solution of methyl 4-heptafluoroisopropyl-3-methylbenzoate (0.4 g, 1.3 mmols) dissolved in methanol (4 ml). The resulting mixture was stirred for about 2 hours, and then hexane and water were added thereto to separate an aqueous layer. The aqueous layer was made to acidify by addition of 3N hydrochloric acid, and then ethyl acetate was added thereto to separate an organic layer. The organic layer was dried with anhydrous sodium sulfate and then concentrated under reduced pressure to obtain the intended product (0.32 g, yield 84%).

Example 12

Preparation of 2-fluoro-4-heptafluoroisopropylbenzoic acid

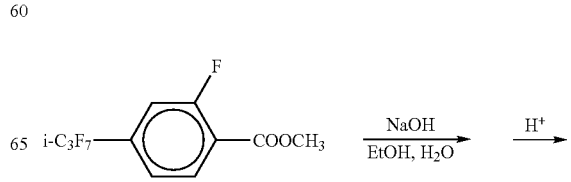

-continued

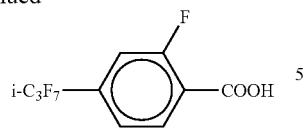

In an ice bath, a solution of sodium hydroxide (0.1 g, 2.5 mmols) dissolved in water (4 ml) was added dropwise to a solution of ethyl 2-fluoro-4-heptafluoroisopropylbenzoate (0.5 g, 1.5 mmols) dissolved in ethanol (4 ml). The resulting mixture was stirred for about 2 hours, and then hexane and water were added thereto to separate an aqueous layer. The aqueous layer was made to acidify by addition of 3N hydrochloric acid, and then ethyl acetate was added thereto to separate an organic layer. The organic layer was dried with anhydrous sodium sulfate, and then concentrated under reduced pressure to obtain the intended product (0.38 g, yield 83%).

In a similar manner, the following compounds were prepared.

2-fluoro-4-heptafluoroisopropylbenzoic acid

Physical property: $^1$H-NMR $\delta(CDCl_3)$; 7.484(d, 1H), 7.52(d, 1H), 8.18(t, 1H), 10.55(brs, 1H).

4-heptafluoroisopropyl-2-methoxybenzoic acid

Physical property: $^1$H-NMR $\delta(CDCl_3)$; 4.124(s, 3H), 7.28 (s, 1H), 7.37(m, 1H), 8.27(d, 1H).
m.p. 96–97° C.

4-heptafluoroisopropyl-2-methylbenzoic acid

Physical property: $^1$H-NMR $\delta(CDCl_3)$; 2.72(s, 3H), 7.53 (s, 1H), 7.54(d, 1H), 8.18(d, 1H).
m.p. 108–109° C.

2,6-dimethyl-4-heptafluoroisopropylbenzoic acid

Physical property: $^1$H-NMR $\delta(CDCl_3)$; 2.505(s, 6H), 7.34 (s, 2H).
m.p. 80–81° C.

3-fluoro-4-heptafluoroisopropylbenzoic acid

Physical property: $^1$H-NMR $\delta(CDCl_3)$; 7.784(t, 1H), 7.94 (d, 1H), 8.05(m, 1H), 11.40(brs, 1H).
$^{19}$F-NMR $\delta(CDCl_3)$; −75.49(6F), −107.54(1F), −178.29 (1F)
m.p. 54–58° C.

4-heptafluoroisopropyl-3-methylbenzoic acid

Physical property: $^1$H-NMR $\delta(CDCl_3)$; 2.62(d, 3H), 7.62 (d, 1H), 8.00(d, 1H), 8.03(s, 1H).
m.p. 129–130° C.

4-heptafluoroisopropyl-2-methylsulfonylbenzoic acid

Physical property: $^1$H-NMR $\delta(CDCl_3)$; 3.45(s, 3H), 7.99 (m, 2H), 8.41(s, 1H), 9.42(brs, 1H).

4. Preparation of Benzoic Acid Halides

Example 13

Preparation of 4-heptafluoroisopropyl-3-methylbenzoyl chloride

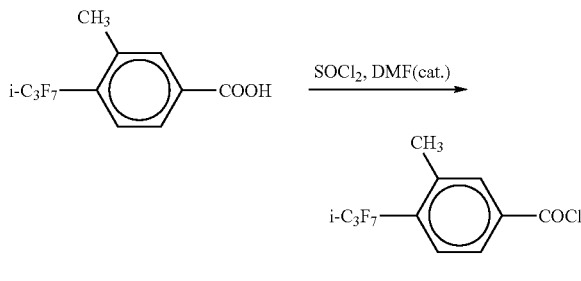

4-Heptafluoroisopropyl-3-methylbenzoic acid (0.32 g, 1.0 mmol) was dissolved in thionyl chloride (3 ml), one drop of dimethylformamide (DMF) was added thereto, and the mixture was heated under reflux for 3 hours. After completion of reaction, the reaction mixture was cooled to room temperature, and thionyl chloride was distilled off under reduced pressure to obtain a crude product of the intended compound.

In a similar manner, the following compounds were prepared.

3-heptafluoroisopropylbenzoyl chloride

Physical property: $^1$H-NMR $\delta(CDCl_3)$; 7.71(t, 1H), 7.94 (d, 1H), 8.33(d, 1H), 8.37(s, 1H).
$^{19}$F-NMR $\delta(CDCl_3)$; −76.04(6F), −182.83(1F).

4-heptafluoroisopropyl-2-methylbenzoyl chloride

Physical property: $^1$H-NMR $\delta(CDCl_3)$; 2.65(s, 3H), 7.555 (s, 1H), 7.615(d, 1H), 8.31(d, 1H).

4-heptafluoroisopropyl-2-methoxybenzoyl chloride

Physical property: $^1$H-NMR $\delta(CDCl_3)$; 3.984(s, 3H), 7.22 (s, 1H), 7.30(d, 1H), 8.15(d, 1H).

4-heptafluoroisopropyl-2-methylthiobenzoyl chloride

Physical property: $^1$H-NMR $\delta(CDCl_3)$; 3.34(s, 3H), 8.04 (s, 1H), 8.40(s, 1H).

4-heptafluoroisopropyl-2-methylsulfonylbenzoyl chloride

Physical property: $^1$H-NMR $\delta(CDCl_3)$; 3.34(s, 3H), 8.04 (s, 2H), 8.40(s, 1H).

4-heptafluoroisopropyl-3-methylbenzoyl chloride

Physical property: $^1$H-NMR $\delta(CDCl_3)$; 2.64(d, 3H), 7.66 (d, 1H), 8.00–8.05(m, 2H).

5. Preparation of Benzamide

Example 14

Preparation of 4-heptafluoroisopropyl-3-methylbenzamide

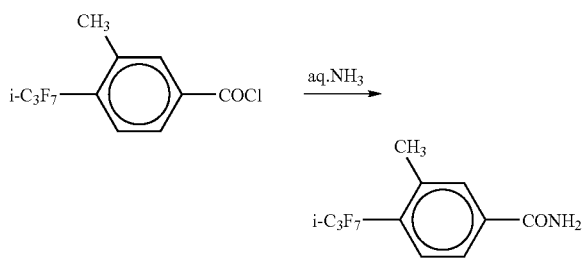

In an ice bath, an aqueous ammonia solution (5 ml) was added to the crude product (0.4 g) of 4-heptafluoroisopropyl-3-methylbenzoyl chloride, and the resulting mixture was stirred for about 30 minutes. Ethyl acetate was added thereto to separate an organic layer, the organic layer was dried with anhydrous sodium sulfate and then concentrated under reduced pressure to obtain the intended product (0.3 g, yield (crude) 98%).

In a similar manner, the following compounds were prepared.

4-heptafluoroisopropyl-2-methylbenzamide

Physical property: $^1$H-NMR $\delta$(CDCl$_3$); 4.03(s, 3H), 7.20 (s, 1H), 7.32(d, 1H), 8.32(d, 1H).
m.p. 104–105° C.

3-fluoro-4-heptafluoroisopropylbenzamide

Physical property: $^1$H-NMR $\delta$(CDCl$_3$); 6.47(brs, 2H), 7.66–7.71(m, 3H).
$^{19}$F-NMR $\delta$(CDCl$_3$); −75.64(6F), −107.53(1F), −178.44 (1F).
m.p. 85–86° C.

4-heptafluoroisopropyl-3-methylbenzamide

Physical property: $^1$H-NMR $\delta$(CDCl$_3$); 2.53(d, 3H), 7.59 (d, 1H), 7.86(d, 1H), 7.90(s, 1H).
m.p. 66–68° C.

6. Preparation of cyanobenzenes

Example 15

Preparation of 1-cyano-4-heptafluoroisopropyl-3-methylbenzene

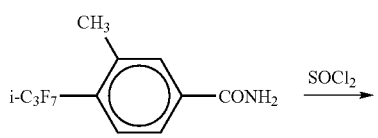

-continued

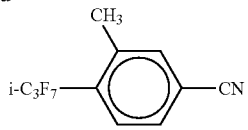

4-Heptafluoroisopropyl-3-methylbenzamide (0.3 g, 1 mmol) was dissolved in thionyl chloride (4 ml) and heated under reflux for 1 hour. The reaction mixture was cooled to room temperature, then thionyl chloride was distilled off under reduced pressure, and the residue was purified by silica gel column chromatography (hexane:ethyl acetate=9:1) to obtain the intended product (0.22 g, yield 78%).

In a similar manner, the following compounds were prepared.

1-cyano-4-heptafluoroisopropyl-2-methylbenzene

Physical property: $^1$H-NMR $\delta$(CDCl$_3$); 2.41(s, 3H), 7.33–7.41(m, 3H).

1-cyano-4-heptafluoroisopropyl-2-methoxybenzene

Physical property: $^1$H-NMR $\delta$(CDCl$_3$); 2.41(s, 3H), 7.33–7.41(m, 3H).

1-cyano-3-fluoro-4-heptafluoroisopropylbenzene

Physical property: $^1$H-NMR $\delta$(CDCl$_3$); 7.55(d, 1H), 7.63 (d, 1H), 7.79(t, 1H).

1-cyano-4-heptafluoroisopropyl-3-methylbenzene

Physical property: $^1$H-NMR $\delta$(CDCl$_3$); 2.59(d, 3H), 7.60 (brs, 3H).

7. Preparation of phenols

Example 16

Preparation of 4-heptafluoroisopropyl-3-methylphenol

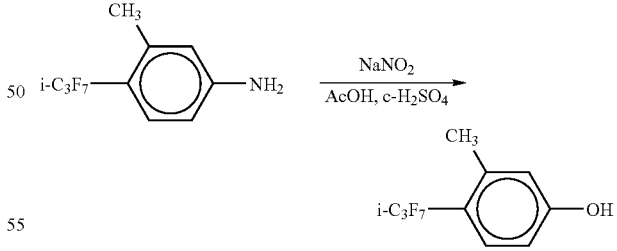

In an ice bath, 4-heptafluoroisopropyl-3-methylaniline (5 g, 18 mmols) was dissolved in glacial acetic acid (25 ml), and concentrated sulfuric acid (3.6 g) was added thereto. Then a solution of sodium nitrite (1.4 g, 20 mmols) dissolved in water (3 ml) was slowly added so that the reaction temperature might be not higher than 0° C. After completion of the addition, the reaction mixture was stirred further for 30 minutes, then water (3 ml) was added thereto, the resulting mixture was heated to about 80° C. and stirred for 5 hours. After completion of reaction, the reaction mixture was cooled to room temperature, hexane was added thereto to separate an organic layer, the organic layer was washed twice with water, once with a saturated aqueous sodium hydrogen carbonate solution and once with a saturated aqueous sodium chloride solution, dried with anhydrous sodium sulfate, concentrated under reduced pressure and purified by silica gel column chromatography (hexane:ethyl acetate=3:1) to obtain the intended product (4.0 g, yield 81%).

In a similar manner the following compounds were prepared.

4-heptafluoroisopropyl-2-methylphenol

Physical property: $^1$H-NMR δ(CDCl$_3$); 3.26(s, 3H), 5.80 (brs, 1H), 6.84(d, 1H), 7.30(d, 1H), 7.33(s, 1H).

4-heptafluoroisopropyl-2-methoxyphenol

Physical property: $^1$H-NMR δ(CDCl$_3$); 3.88 (s, 3H), 6.74(d, 1H), 6.94(s, 1H), 6.96(d, 1H).

4-heptafluoroisopropyl-3-methylphenol

Physical property: $^1$H-NMR δ(CDCl$_3$); 2.46(s, 1H), 5.19 (s, 1H), 6.74(brs, 2H), 7.44(d, 1H).
nD 1.4242 (24.1° C.)

2,6-dimethoxy-4-heptafluoroisopropylphenol

Physical property: $^1$H-NMR δ(CDCl$_3$); 3.89(s, 3H), 3.94 (s, 6H), 5.82(s, 1H), 6.785(s, 2H).

2,6-dimethyl-4-heptafluoroisopropylphenol

Physical property: $^1$H-NMR δ(CDCl$_3$); 2.26(s, 6H), 5.3 (brs, 1H), 7.19(s, 2H).

8. Preparation of benzenesulfonyl halides

Example 17

Preparation of 4-heptafluoroisopropyl-3-methylbenzenesulfonyl chloride

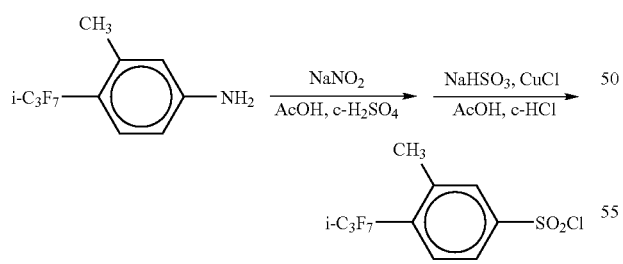

In an ice bath, 4-heptafluoroisopropyl-3-methylaniline (5 g, 18.2 mmols) was dissolved in glacial acetic acid (5 ml) and further, concentrated hydrochloric acid (15 ml) was added thereto. Then, a solution of sodium nitrite (1.4 g, 20 mmols) dissolved in water (3 ml) was slowly added so that the reaction temperature might be not higher than 0° C. After completion of the addition, the reaction mixture was stirred further for 20 minutes. The resulting diazonium salt solution was slowly added to a separately prepared mixture of sodium hydrogen sulfite (5.3 g, 51 mmols), copper chloride (0.35 g, 3.5 mmols), glacial acetic acid (34 ml) and concentrated hydrochloric acid (7 ml) at room temperature. The resulting mixture was stirred at room temperature for 2.5 hours, then hexane was added thereto to separate an organic layer, the organic layer was dried with anhydrous sodium sulfate and then concentrated under reduced pressure to obtain the intended product (4.4 g, yield 67%).

In a similar manner, the following compounds were prepared.

4-heptafluoroisopropyl-2-methylbenzenesulfonyl chloride

Physical property: $^1$H-NMR δ(CDCl$_3$); 2.88(s, 3H), 7.69 (brs, 2H), 8.21(d, 1H).

4-heptafluoroisopropyl-2-methoxybenzenesulfonyl chloride

Physical property: $^1$H-NMR δ(CDCl$_3$); 4.125(s, 3H), 7.34 (s, 1H), 7.35(d, 1H), 8.10(d, 1H).

3-fluoro-4-heptafluoroisopropylbenzenesulfonyl chloride

Physical property: $^1$H-NMR δ(CDCl$_3$); 7.89–8.03(m, 3H).
$^{19}$F-NMR δ(CDCl$_3$); −75.23(6F), −177.9(1F)

4-heptafluoroisopropyl-3-methylbenzenesulfonyl chloride

Physical property: $^1$H-NMR δ(CDCl$_3$); 2.69(d, 3H), 7.77 (d, 1H), 7.95(d, 1H), 7.97(s, 1H).

2,6-dimethyl-4-heptafluoroisopropylbenzenesulfonyl chloride

Physical property: $^1$H-NMR δ(CDCl$_3$); 2.09(s, 6H), 7.32 (d, 2H).

9. Preparation of sulfonamides

Example 18

Preparation of 3-fluoro-4-heptafluoroisopropylbenzenesulfonamide

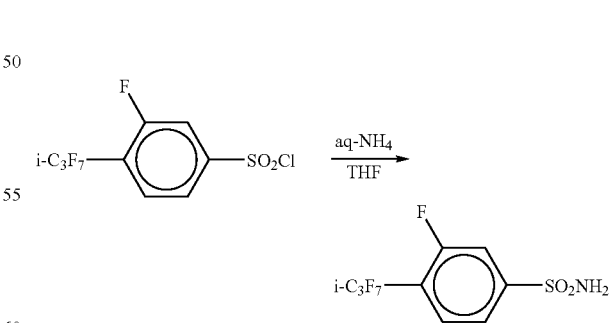

Into 20 ml of tetrahydrofuran (THF) containing 1.0 g of aqueous 28% ammonia solution was added dropwise, with ice cooling, 2 ml of a THF solution of 0.6 g (1.65 mmols) of 3-fluoro-4-heptafluoroisopropylbenzenesulfonyl chloride. The resulting solution was stirred at room temperature for 2 hours, then poured into water, and the intended product was extracted with ethyl acetate. The liquid extract was washed with a saturated aqueous sodium chloride solution, then dried, the solvent was distilled off under reduced pressure, and the residue obtained was purified by silica gel column chromatography to obtain 0.5 g of the intended product.

Physical property: $^1$H-NMR δ(CDCl); 7.76(brs, 2H), 7.91–7.95(m, 2H), 8.06(t, 1H).

In a similar manner, the following compound was obtained.

4-heptafluoroisopropyl-3-methylbenzenesulfonamide

Physical property: $^1$H-NMR δ(CDCl$_3$); 2.62(d, 3H), 4.87 (brs, 2H), 7.65(d, 1H), 7.83(d, 1H), 7.86(d, 1H).

10. Preparation of phenylhydrazines

Example 18

Preparation of 2,6-dimethyl-4-heptafluoroisopropylphenylhydrazine hydrochloride

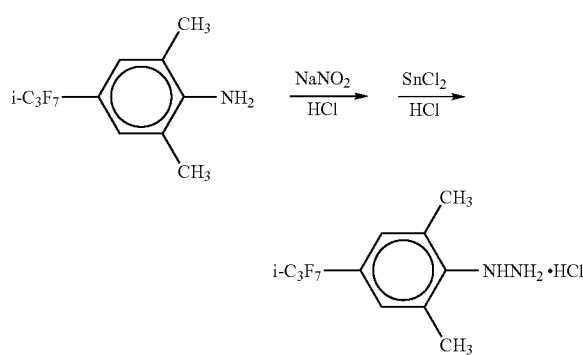

2,6-Dimethyl-4-heptafluoroisopropylaniline (10 g, 34.7 mmols) was added into hydrochloric acid (30 ml), and an aqueous solution (24 ml) of sodium nitrite (2.6 g, 2 mmols) was dropwise added thereto at a temperature not higher than 5° C. After 15 minutes of further stirring, the resulting diazonium salt solution was added dropwise at room temperature to an aqueous hydrochloric acid solution (85 ml) containing anhydrous tin chloride (20.4 g, 108 mmols). The precipitated cake-like solid was collected by filtration and washed successively with water and hexane to obtain the intended product (8.5 g, yield 72%).

Physical property: $^1$H-NMR δ(CDCl$_3$); 2.474(s, 6H), 7.37 (s, 2H), 9.99(brs, 2H).

$^{19}$F-NMR δ(CDCl$_3$); −70.81(d, 7F), −177.36(m, 1F).

In a similar manner, the following compounds were obtained.

4-heptafluoroisopropyl-2-methylphenylhydrazine

Physical property: $^1$H-NMR δ(CDCl$_3$); 2.13(s, 3H), 3.41 (brs, 2H), 5.30(brs, 1H), 7.04(d, 1H), 7.23(s, 1H), 7.59(d, 1H).

2,6-dichloro-4-heptafluoroisopropylphenylhydrazine

Physical property: $^1$H-NMR δ(CDCl$_3$); 4.06(brs, 2H), 5.83(brs,1H), 7.47(s, 2H).

$^{19}$F-NMR δ(CDCl$_3$); −76.23(6F), −182.45(1F)

11. Preparation of isocyanates

Example 19

Preparation of 4-heptafluoroisopropylphenyl isocyanate

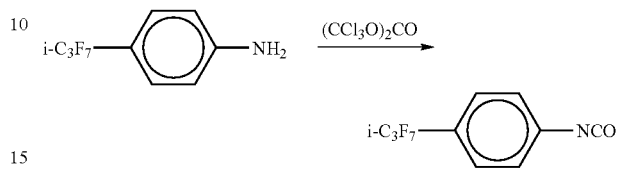

A toluene solution (5 ml) containing 4-heptafluoroisopropylaniline (3 g, 10.9 mmols) was dropwise added to a toluene solution (70 ml) containing triphosgene (1.1 g, 3.6 mmols) while the reaction mixture was being warmed. After completion of the addition, the reaction liquid was heated under reflux for 4 hours, then the solvent was distilled off under reduced pressure, hexane was added to the resulting residue to form a suspension, which was then fittered, and the filtrate obtained was concentrated to obtain the intended product (3 g).

In a similar manner, the following compound was obtained.

4-heptafluoroisopropyl-2-methoxyisocyanate

Physical property: $^1$H-NMR δ(CDCl$_3$); 3.895(s, 3H), 7.07 (s, 1H), 7.10–7.16(m, 2H).

m.p. 38–39° C.

12. Preparation of benzaldehydes 2-heptafluoroisopropylbenzaldehyde

Physical property: $^1$H-NMR δ(CDCl$_3$); 7.68(m, 3H), 8.04 (m, 1H), 10.48(d, 1H)

13. Preparation of isothiocyanates

Example 20

Preparation of 4-heptafluoroisopropyl-2-methoxyphenyl isothiocyanate

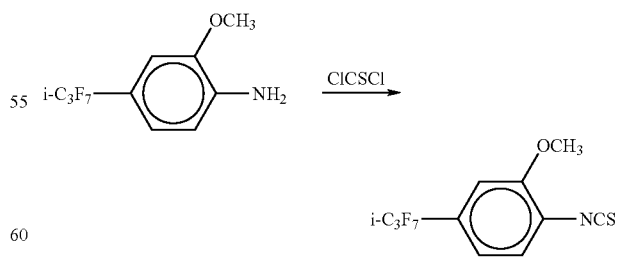

Thiophosgene (1.3 g, 11.5 mmols) was added dropwise at room temperature to a solution of 4-heptafluoroisopropyl-2-methoxyaniline (1.3 g, 11.5 mmols) dissolved in toluene (100 ml), the resulting mixture was heated under reflux for 2 hours, then brought back to room temperature, and the solvent was distilled off under reduced pressure to obtain the intended product (3.3 g, 10.9 mmols).

Physical property: $^1$H-NMR $\delta$(CDCl$_3$); 3.96(s, 3H), 7.10 (s, 1H), 7.11–7.22(m, 2H).

14. Preparation of acetophenones

Example 21

Preparation of 4-heptafluoroisopropylacetophenone

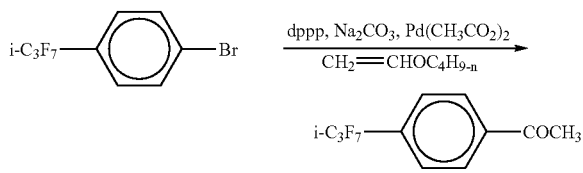

To n-butanol (50 ml) were added 1-bromo-4-heptafluoroisopropylbenzene (8.0 g, 24.6 mmols), n-butylvinyl ether (11.1 mmols), sodium carbonate (11.7 g, 111 mmols), dppp (1,3-bis(diphenylphosphino)propane, 0.87 g, 1.8 mmols) and palladium acetate (0.28 g, 17.4 mmols), and the resulting mixture was heated under reflux for 11 hours. The reaction liquid was brought back to room temperature, filtered, the filtrate obtained was concentrated, an aqueous 3N hydrochloric acid (40 ml) was added to the residue, the resulting mixture was stirred vigorously for 30 minutes, then extracted with hexane, the organic layer was washed with a saturated aqueous sodium chloride solution, the solvent was distilled off under reduced pressure, and the residue obtained was purified by silica gel column chromatography to obtain the intended product (5.6 g, yield 79%).

Physical property: $^1$H-NMR $\delta$(CDCl$_3$); 2.65(s, 3H), 7.74 (d, 2H), 8.08(d, 2H).

nD 1.4341 (21.5° C.)

In a similar manner, the following compounds were obtained.

2,6-dimethyl-4-heptafluoroisopropylacetophenone

Physical property: $^1$H-NMR $\delta$(CDCl$_3$); 2.31(s, 6H), 2.50 (s, 3H), 7.25(s, 2H).
$^{19}$F-NMR $\delta$(CDCl$_3$); −76.06(6F), −183.33(1F).

3-fluoro-4-heptafluoroisopropylacetophenone

Physical property: $^1$H-NMR $\delta$(CDCl$_3$); 2.64(s, 3H), 7.73–7.79(m, 2H), 7.86(m, 1H).

4-heptafluoroisopropyl-3-methylacetophenone

Physical property: $^1$H-NMR $\delta$(CDCl$_3$); 2.61(d, 3H), 2.624(s, 3H), 7.60(d, 1H), 7.83(d, 1H), 7.85(s, 1H).

4-heptafluoroisopropyl-2-methylacetophenone

Physical property: $^1$H-NMR $\delta$(CDCl$_3$); 2.565(s, 3H), 2.60 (s, 3H), 7.49(s, 1H), 7.504(d, 1H), 7.76(d, 1H).

15. Preparation of diazonium Salt 4-heptafluoroisopropyl-3-methylphenyldiazonium tetrafluoroborate Physical property: $^1$H-NMR $\delta$(CDCl$_3$); 2.675(d, 3H), 8.25(d, 1H), 8.74(d, 1H), 8.81(s, 1H).

$^{19}$F-NMR $\delta$(CDCl$_3$); −69.40(6F), −143.99(4F), −174.51 (1F).

The prefluoroisopropylbenzene derivative of this invention can be used, for example, for producing the following compound, which exhibits pesticidal activity.

Reference Example 1

Preparation of 1,1-dimethyl-3-(4-heptafluoroisopropylphenyl)urea

A tetrahydrofuran solution (2 ml) containing 4-heptafluoroisopropylphenyl isocyanate (1 g, 3.5 mmols) was added into tetrahydrofuran (15 ml) containing dimethylamine (50% aq., 0.38 g, 4.2 mmols) at room temperature. The resulting reaction mixture was stirred further for 2 hours, then poured into water, extracted with ethyl acetate, the organic layer was washed with a saturated aqueous sodium chloride solution, then the solvent was distilled off under reduced pressure, and the residue obtained was purified by column chromatography to obtain the intended product (0.84 g, yield 75%).

Physical property: m.p. 151.4–154.2° C.

Reference Example 2

Test for herbicidal effect on paddy field weeds pre-emergence

Soil was filled into 1/10000 are pots and brought into a state of paddy field, in which seeds of barnyard grass (*Echinochloa crus-galli* Beauv.) and bulrush (*Scirpus juncoides* Roxb.) were made to be before germination. The soil in the pots were treated with a solution containing a predetermined dosage of a chemical agent comprising a compound obtained in Reference Example 1 as the active ingredient.

Twenty one days after the treatment, the herbicidal effect was investigated, the result was compared with that in untreated plot to calculate the weedkilling rate, and the herbicidal effect was judged according to the following criterion.

Criterion for herbicidal effect:
5 - - - Weedkilling rate is 100%.
4 - - - Weedkilling rate is 90–99%.
3 - - - Weedkilling rate is 70–89%.
2 - - - Weedkilling rate is 40–69%.
1 - - - Weedkilling rate is 1–39%.
0 - - - Weedkilling rate is 0%.

At the same time, phytotoxicity on paddy rice was investigated, and judged according to the following criterion.

Criterion for phytotoxicity on paddy rice:
5 - - - Weedkilling rate is 100%.
4 - - - Weedkilling rate is 90–99%.
3 - - - Weedkilling rate is 70–89%.
2 - - - Weedkilling rate is 40–69%.
1 - - - Weedkilling rate is 21–39%.
0 - - - Weedkilling rate is 0–20 (No phytotoxicity).

As a result, herbicidal effects on barnyard grass (*Echinochloa crus-galli* Beauv.) and bulrush (*Scirpus juncoides* Roxb.) were rated "4" and "2" at the dosage of 5 kg/ha, and there was no phytotoxicity (rated "0") on the paddy rice treated.

Reference Example 3

Herbicidal effect on upland weeds pre-emergence

Polyethylene-made vats having a size of 10 cm (length)× 20 cm (width)×5 cm (height) were filled with soil, sown with seeds of *Arabidopsis thialiana*, bent grass (*Agrostis spp.*) and monochoria (*Monochoria veginalis*), and with seeds of wheat and soybean plant as upland crop plants, and then covered with soil. Then, a liquid preparation of an agent comprising a prescribed concentration of a compound obtained in Reference Example 1 as active ingredient was sprayed.

Fourteen days after the treatment, the herbicidal effect was investigated, from which weed-killing rate was calculated in the same manner as in Reference Example 2, and the herbicidal effect was judged.

At the same time, phytotoxicity on soybean plant and wheat was investigated and judged according to the criterion mentioned in Reference Example 1.

As a result, herbicidal effects on *Arabidopsis thaliana* and monochoria (*Monochoria veginalis*) were rated "5", and that of bent grass (*Agrostis* spp.) was rated "4" respectively, at the dosage of 5 kg/ha. Further, there was no phytotoxicity (rated "0") on the wheat and soybean plant treated.

Reference Example 4

Herbicidal effect on upland weeds after emergence

Polyethylene-made vats having a size of 10 cm (length)× 20 cm (width)×5 cm (height) were filled with soil, sown with the seeds of the upland weeds mentioned below and with seeds of soybean plant and wheat as upland crop plants, and then covered with soil. The plants were made to grow up until they reached the 1 to 2 leaved stage, after which an agent comprising a prescribed concentration of a compound obtained in Reference Example 1 as active ingredient was sprayed.

Fourteen days after the treatment, the herbicidal effect was investigated, from which weed-killing rate was calculated in the same manner as in Reference Example 2 and the results were judged. At the same time, phytotoxicity on soybean plant and wheat was investigated and judged in the same manner as in Reference Example 2.

As a result, herbicidal effect on *Arabidopsis thaliana* was rated "5" and those of bent grass (*Agrostis* spp.) and monochoria (*Monochoria veginalis*) were rated "3" respectively, at the dosage of 5 kg/ha. Further, there was no phytotoxicity (rated "0") on the wheat and soybean plant treated.

The invention claimed is:

1. A perfluoroisopropylbenzene derivative represented by the formula (I) or salts thereof:

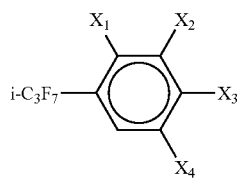

(I)

wherein $X_1$ is a hydrogen atom, halogen atom, formyl group, $(C_1-C_6)$alkyl group, halo$(C_1-C_6)$alkyl group, $(C_1-C_6)$alkoxy group, $(C_1-C_6)$alkylthio group, hydroxy$(C_1-C_6)$alkyl group or $(C_1-C_6)$alkylcarbonyloxy$(C_1-C_6)$alkyl group; $X_2$ is a hydrogen atom, halogen atom, formyl group, hydroxy group, $(C_1-C_6)$alkyl group, halo$(C_1-C_6)$alkyl group, $(C_1-C_6)$alkoxy group, $(C_1-C_6)$alkylthio group, $(C_1-C_6)$alkylsulfinyl group, $(C_1-C_6)$alkylsulfonyl group, hydroxy$(C_1-C_6)$alkyl group or —C(=O)—$R_1$ (wherein $R_1$ is a hydrogen atom, halogen atom, hydroxy group, $(C_1-C_6)$ alkyl group, $(C_1-C_6)$alkoxy group or $NR_2R_3$ (wherein $R_2$ and $R_3$ may be the same or different and are each a hydrogen atom, $(C_1-C_6)$alkyl group or $(C_1-C_6)$alkoxy group)); $X_3$ is a hydrogen atom, halogen atom, hydroxy group, cyano group, isocyanate group, isothiocyanate group, hydrazino group, diazo group, mercapto group, $(C_1-C_6)$alkoxy group, $(C_1-C_6)$alkylthio group, —C(=O)—$R_1$ (wherein $R_1$ is the same as defined above) or —$SO_2$—$R_4$ (wherein $R_4$ is a halogen atom, hydroxy group, $(C_1-C_6)$alkyl group or $NR_5R_6$ (wherein $R_5$ and $R_6$ may be the same or different and are each a hydrogen atom or $(C_1-C_6)$alkyl group)); and $X_4$ is a hydrogen atom, halogen atom, $(C_1-C_6)$alkyl group or $(C_1-C_6)$alkoxy group; provided that (1) when $X_1$, $X_2$ and $X_4$ are each a hydrogen atom, then $X_3$ is not a hydroxycarbonyl group or methoxycarboxyl group, (2) when $X_1$ and $X_4$ are each a hydrogen atom and $X_2$ is a formyl group, then $X_3$ is not a methoxy group, (3) when any one of $X_1$, $X_2$ and $X_3$ is a methoxy group, then $X_4$ and the remaining two of $X_1$, $X_2$ and $X_3$ are not each a hydrogen atom, (4) when any one of $X_2$ and $X_3$ is a hydroxyl group, then $X_1$, $X_4$ and the remaining one of $X_2$ and $X_3$ are not each a hydrogen atom, (5) when any one of $X_1$, $X_2$, $X_3$ and $X_4$ is a fluorine atom, then the remaining three of $X_1$, $X_2$, $X_3$ and $X_4$ are not each a hydrogen atom, (6) when $X_1$, $X_2$ and $X_4$ are each a hydrogen atom, then $X_3$ is not a chlorine atom, bromine atom or iodine atom, (7) when any one of $X_1$, $X_2$, $X_3$ and $X_4$ is a methyl group, then the remaining three of $X_1$, $X_2$, $X_3$ and $X_4$ are not each a hydrogen atom, (8) when $X_1$, $X_2$ and $X_4$ are each a hydrogen atom, then $X_3$ is not an isopropyl group or chloromethyl group, (9) when $X_1$, $X_3$ and $X_4$ are each a hydrogen atom, then $X_2$ is not a trifluoromethyl group,

(10) when $X_1$ and $X_4$ are each a methyl group and $X_2$ is a hydrogen atom, then $X_3$ is not a hydrogen atom or heptafluoroisopropyl group,

(11) when $X_1$ and $X_3$ are each a hydrogen atom and any one of $X_2$ and $X_4$ is a hydrogen atom, then the remaining one of $X_2$ and $X_4$ is not a heptafluoroisopropyl group,

(12) when $X_1$ is a hydrogen atom, $X_3$ is a hydroxycarbonyl group, and any one of $X_2$ and $X_4$ is a hydrogen atom, then the remaining one of $X_2$ and $X_4$ is not a heptafluoroisopropyl group,

(13) when $X_1$, $X_2$ and $X_4$ are each a hydrogen atom, then $X_3$ is not a chlorocarbonyl group,

(14) when any three of $X_1$, $X_2$, $X_3$ and $X_4$ are each a hydrogen atom, then the remaining one of $X_1$, $X_2$, $X_3$ and $X_4$ is not a hydrogen atom or nitro group,

(15) when $X_3$ is a hydrogen atom, any two of $X_1$, $X_2$ and $X_4$ are each a hydrogen atom, then the remaining one of $X_1$, $X_2$ and $X_4$ is not a methoxycarbonyl group,

(16) when $X_1$, $X_2$ and $X_4$ are each a hydrogen atom, then $X_3$ is not a heptafluoroisopropyl group,

(17) when $X_3$ and $X_4$ are each a hydrogen atom, any one of $X_1$ and $X_2$ is a hydrogen atom, then the remaining one of $X_1$ and $X_2$ is not an iodine atom,

(18) each of $X_1$, $X_2$, $X_3$ and $X_4$ does not simultaneously represent a fluorine atom,

(19) when $X_1$ is a hydrogen atom, any two of $X_2$, $X_3$, and $X_4$ are each a hydrogen atom, then the remaining one of $X_2$, $X_3$ and $X_4$ is not a 2,2,2-trifluoro-1-trifluoromethylethyl group, and

(20) when $X_1$ and $X_3$ are each a hydrogen atom, any one of $X_2$ and $X_4$ is a hydrogen atom, then the remaining one of $X_2$ and $X_4$ is not a bromine atom or hydroxycarbonyl group.

2. The perfluoroisopropylbenzene derivative or the salts thereof according to claim 1, wherein $X_1$ is a formyl group, $(C_1–C_6)$alkyl group, halo$(C_1–C_6)$alkyl group, hydroxy$(C_1–C_6)$alkyl group or $(C_1–C_6)$alkylcarbonyloxy$(C_1–C_6)$alkyl group; and $X_2$, $X_3$ and $X_4$ are each a hydrogen atom.

3. The perfluoroisopropylbenzene derivative or the salts thereof according to claim 1, wherein $X_1$, $X_3$ and $X_4$ are each a hydrogen atom; and $X_2$ is a $(C_1–C_6)$alkyl group, halo$(C_1–C_6)$alkyl group, hydroxy$(C_1–C_6)$alkyl group, $(C_1–C_6)$alkyl carbonyl group or —C(=O)—$R_1$ (wherein $R_1$ is a hydrogen atom, halogen atom, $(C_1–C_6)$alkyl group, $(C_2–C_6)$alkoxy group, or $NR_2R_3$ (wherein $R_2$ and $R_3$ may be the same or different and are each a hydrogen atom, $(C_1–C_6)$alkyl group or $(C_1–C_6)$alkoxy group)), provided that $X_2$ is not a heptafluoroisopropyl group, or 2,2,2-trifluoro-1-trifluoromethylethyl group.

4. The perfluoroisopropylbenzene derivative or the salts thereof according to claim 1, wherein $X_1$, $X_2$ and $X_4$ are each a hydrogen atom; and $X_3$ is an isocyanate group, isothiocyanate group or $(C_1–C_6)$alkylcarbonyl group.

5. The perfluoroisopropylbenzene derivative or the salts thereof according to claim 1, wherein $X_1$ and $X_4$ are each a hydrogen atom; $X_2$ is a hydroxy group, $(C_1–C_6)$alkyl group or $(C_1–C_6)$alkoxy group; and $X_3$ is a halogen atom, hydroxy group, cyano group, isocyanate group, isothiocyanate group, hydrazino group, —C(=O)—$R_1$ (wherein $R_1$ is a hydrogen atom, hydroxy group, halogen atom, $(C_1–C_6)$alkyl group, $(C_1–C_6)$alkoxy group or $NR_2R_3$ (wherein $R_2$ and $R_3$ may be the same or different and are each a hydrogen atom, $(C_1–C_6)$ alkyl group or $(C_1–C_6)$alkoxy group)) or —$SO_2$—$R_4$ (wherein $R_4$ is a halogen atom, hydroxy group or $NR_5R_6$ (wherein $R_5$ and $R_6$ may be the same or different and are each a hydrogen atom or $(C_1–C_6)$alkyl group)).

6. The perfluoroisopropylbenzene derivative or the salts thereof according to claim 1, wherein $X_1$ and $X_4$ are each a hydrogen atom; $X_2$ is a halogen atom; and $X_3$ is a halogen atom or —C(=O)—$R_1$ (wherein $R_1$ is a halogen atom, hydroxy group, $(C_1–C_6)$alkyl group, $(C_1–C_6)$alkoxy group or $NR_2R_3$ (wherein $R_2$ and $R_3$ may be the same or different and are each a hydrogen atom or $(C_1–C_6)$alkyl group)).

7. The perfluoroisopropylbenzene derivative or the salts thereof according to claim 1, wherein $X_1$ is a halogen atom or $(C_1–C_6)$alkyl group; $X_2$ and $X_4$ are each a hydrogen atom; and $X_3$ is a halogen atom, hydroxy group, cyano group, diazo group, —C(=O)—$R_1$ (wherein $R_1$ is a halogen atom, hydroxy group, $(C_1–C_6)$alkyl group, $(C_1–C_6)$alkoxy group or $NR_2R_3$ (wherein $R_2$ and $R_3$ may be the same or different and are each a hydrogen atom or $(C_1–C_6)$alkyl group)) or $SO_2$—$R_4$ (wherein $R_4$ is a halogen atom, hydroxy group or $NR_5R_6$ (wherein $R_5$ and $R_6$ may be the same or different and are each a hydrogen atom or $(C_1–C_6)$alkyl group)).

8. The perfluoroisopropylbenzene derivative or the salts thereof according to claim 1, wherein $X_2$ and $X_4$ are each a hydrogen atom; $X_1$ is a $(C_1–C_6)$alkylthio group; and $X_3$ is a halogen atom or —C(=O)—$R_1$ (wherein $R_1$ is a halogen atom, hydroxy group or $(C_1–C_6)$alkoxy group).

9. The perfluoroisopropylbenzene derivative or the salts thereof according to claim 1, wherein $X_1$ is a hydrogen atom; $X_2$ and $X_4$ are each a $(C_1–C_6)$alkyl group; and $X_3$ is a halogen atom, hydrazine group, —C(=O)—$R_1$ (wherein $R_1$ is a halogen atom, hydroxy group, $(C_1–C_6)$alkyl group, $(C_1–C_6)$alkoxy group or $NR_2R_3$ (wherein $R_2$ and $R_3$ may be the same or different and are each a hydrogen atom or $(C_1–C_6)$alkyl group)) or —$SO_2$—$R_4$ (wherein $R_4$ is a halogen atom, hydroxy group or $NR_5R_6$ (wherein $R_5$ and $R_6$ are the same as defined above)).

10. The perfluoroisopropylbenzene derivative and the salts thereof according to claim 1, wherein $X_1$ is a hydrogen atom; $X_2$ and $X_4$ are each a methoxy group; and $X_3$ is a hydroxy group.

11. The perfluoroisopropylbenzene derivative and the salts thereof according to claim 1, wherein $X_2$, $X_3$ and $X_4$ are each a hydrogen atom; and $X_1$ is a formyl group, hydroxymethyl group, chloromethyl group, bromomethyl group or acetoxymethyl group.

12. The perfluoroisopropylbenzene derivative and the salts thereof according to claim 1, wherein $X_1$, $X_3$ and $X_4$ are each a hydrogen atom; and $X_2$ is a formyl group, ethyl group, chloromethyl group, hydroxymethyl group, acetyl group or N-methoxy-N-methylaminocarboxyl group.

13. The perfluoroisopropylbenzen derivative or the salts thereof according to claim 1, wherein $X_1$, $X_2$ and $X_4$ are each a hydrogen atom; and $X_3$ is an isocyanate group or acetyl group.

14. The perfluoroisopropylbenzene derivative or the salts thereof according to claim 1, wherein $X_1$ and $X_4$ are each a hydrogen atom; $X_2$ is a methyl group; and $X_3$ is a chlorine atom, bromine atom, iodine atom, hydroxy group, cyano group, isothiocyanate group, hydrazino group, —C(=O)—$R_1$ (wherein $R_1$ is a hydrogen atom, chlorine atom, hydroxy group, methoxy group or amino group) or —$SO_2$—$R_4$ (wherein $R_4$ is a chlorine atom or amino group).

15. The perfluoroisopropylbenzene derivative or the salts thereof according to claim 1, wherein $X_1$ and $X_4$ are each a hydrogen atom; $X_2$ is a methoxy group; and $X_3$ is a chlorine atom, bromine atom, iodine atom, cyano group, hedroxy group, mercapto group, isocyanate group, isothiocyanate group, —C(=O)—$R_1$ (wherein $R_1$ is a hydrogen atom, chlorine atom, methoxy group, hydroxy group or amino group) or —$SO_2$—$R_4$ (wherein $R_4$ is a chlorine atom or amino group).

16. The perfluoroisopropylbenzene derivative or the salts thereof according to claim 1, wherein $X_1$ and $X_4$ are each a hydrogen atom; $X_2$ is a fluorine atom; and $X_3$ is a bromine atom or —C(=O)—$R_1$ (wherein $R_1$ is a chlorine atom, hydroxy group, methoxy group or ethoxy group).

17. The perfluoroisopropylbenzene derivative or the salts thereof according to claim 1, wherein $X_2$ and $X_4$ are each a hydrogen atom; $X_1$ is a methyl group; and $X_3$ is a bromine atom, hydroxy group, cyano group, diazo group, —C(=O)—$R_1$ (wherein $R_1$ is a chlorine atom, hydroxy group, methyl group, methoxy group or amino group) or —$SO_2$—$R_4$ (wherein $R_4$ is a chlorine atom or amino group).

18. The perfluoroisopropylbenzene derivative or the salts thereof according to claim 1, wherein $X_2$ and $X_4$ are each a hydrogen atom; $X_1$ is a fluorine atom; and $X_3$ is a chlorine atom, bromine atom, cyano group, —C(=O)—$R_1$ (wherein $R_1$ is a chlorine atom, hydroxy group, methyl group, methoxy group or amino group) or —$SO_2$—$R_4$ (wherein $R_4$ is a chlorine atom or amino group).

19. The perfluoroisopropylbenzene derivative or the salts thereof according to claim 1, wherein $X_2$ and $X_4$ are each a hydrogen atom; $X_1$ is a methylthio group; and $X_3$ is a bromine atom, iodine atom or —C(=O)—$R_1$ (wherein $R_1$ is a chlorine atom, hydroxy group or methoxy group).

20. The perfluoroisopropylbenzene derivative or the salts thereof according to claim 1, wherein $X_1$ is a hydrogen atom; $X_2$ and $X_4$ are each a methyl group; and $X_3$ is a chlorine atom, bromine atom, iodine atom, carboxyl group, methoxycarbonyl group, acetyl group, hydrazino group or —$SO_2$—$R_4$ (wherein $R_4$ is a chlorine atom or amino group).

21. The perfluoroisopropylbenzene derivative or the salts thereof according to claim 1, wherein $X_1$ is a hydrogen atom, $X_2$ and $X_4$ are each a methoxy group and $X_3$ is a hydroxy group.

* * * * *